US010179191B2

(12) United States Patent
Seyedin et al.

(10) Patent No.: US 10,179,191 B2
(45) Date of Patent: Jan. 15, 2019

(54) FLEXIBLE TISSUE MATRIX AND METHODS FOR JOINT REPAIR

(71) Applicant: ISTO Technologies, Inc., St. Louis, MO (US)

(72) Inventors: Mitchell S. Seyedin, St. Louis, MO (US); Anthony J. Ward, St. Louis, MO (US)

(73) Assignee: Isto Technologies II, LLC, St. Louis, MO (US)

( * ) Notice: Subject to any disclaimer, the term of this patent is extended or adjusted under 35 U.S.C. 154(b) by 0 days.

(21) Appl. No.: 14/510,917

(22) Filed: Oct. 9, 2014

(65) Prior Publication Data
US 2016/0101213 A1 Apr. 14, 2016

(51) Int. Cl.
| A61L 27/18 | (2006.01) |
| A61L 27/44 | (2006.01) |
| A61L 27/36 | (2006.01) |
| A61L 27/20 | (2006.01) |
| A61L 27/54 | (2006.01) |
| A61L 27/22 | (2006.01) |
| A61L 27/38 | (2006.01) |
| A61L 27/48 | (2006.01) |

(52) U.S. Cl.
CPC .......... *A61L 27/3608* (2013.01); *A61L 27/20* (2013.01); *A61L 27/227* (2013.01); *A61L 27/3817* (2013.01); *A61L 27/3834* (2013.01); *A61L 27/48* (2013.01); *A61L 27/54* (2013.01); *A61L 2300/414* (2013.01); *A61L 2300/64* (2013.01)

(58) Field of Classification Search
CPC ...... A61L 27/20; A61L 27/54; A61L 27/3608; A61L 2300/64; A61L 27/3834; A61L 2300/414; A61L 27/227; A61L 27/3817; A61L 27/48; C08L 67/04
See application file for complete search history.

(56) References Cited

U.S. PATENT DOCUMENTS

| RE29,321 E | 7/1977 | Holbrook |
| 4,438,102 A | 3/1984 | Ganci |
| 4,440,680 A | 4/1984 | Cioca |
| 4,692,371 A | 9/1987 | Morman et al. |
| 4,789,663 A | 12/1988 | Wallace et al. |
| 4,818,633 A | 4/1989 | Dinwoodie et al. |
| 4,846,835 A | 7/1989 | Grande |
| 4,904,259 A | 2/1990 | Itay |
| 4,957,744 A | 9/1990 | della Valle et al. |
| 5,053,050 A | 10/1991 | Itay |
| 5,139,527 A | 8/1992 | Redl et al. |
| 5,206,023 A | 4/1993 | Hunziker |
| 5,290,552 A | 3/1994 | Sierra et al. |
| 5,368,858 A | 11/1994 | Hunziker |
| 5,475,052 A | 12/1995 | Rhee et al. |
| 5,565,519 A | 10/1996 | Rhee et al. |
| 5,597,897 A | 1/1997 | Ron et al. |
| 5,644,049 A | 7/1997 | Giusti et al. |
| 5,700,289 A | 12/1997 | Breitbart et al. |
| 5,723,508 A | 3/1998 | Healy et al. |
| 5,736,372 A | 4/1998 | Vacanti et al. |
| 5,769,899 A | 6/1998 | Schwartz et al. |
| 5,842,477 A | 12/1998 | Naughton et al. |
| 5,853,746 A | 12/1998 | Hunziker |
| 5,855,608 A | 1/1999 | Brekke et al. |
| 5,891,455 A | 4/1999 | Sittinger et al. |
| 5,916,585 A | 6/1999 | Cook et al. |
| 5,972,385 A | 10/1999 | Liu et al. |
| 6,051,701 A | 4/2000 | Cialdi et al. |
| 6,060,053 A | 5/2000 | Atala |
| 6,193,991 B1 | 2/2001 | Shukla |
| 6,224,893 B1 | 5/2001 | Langer et al. |
| 6,281,256 B1 | 8/2001 | Harris et al. |
| 6,303,585 B1 | 10/2001 | Spiro et al. |
| 6,328,765 B1 | 12/2001 | Hardwick et al. |
| 6,339,074 B1 | 1/2002 | Cialdi et al. |
| 6,344,488 B1 | 2/2002 | Chenite et al. |
| 6,355,699 B1* | 3/2002 | Vyakarnam ............ A61L 15/26 424/443 |
| 6,378,527 B1 | 4/2002 | Hungerford et al. |
| 6,395,253 B2 | 5/2002 | Levy et al. |
| 6,454,811 B1 | 9/2002 | Sherwood et al. |
| 6,514,522 B2 | 2/2003 | Domb |
| 6,534,084 B1 | 3/2003 | Vyakarnam et al. |

(Continued)

FOREIGN PATENT DOCUMENTS

| CA | 2441994 A1 | 10/2002 |
| CA | 2445356 A1 | 4/2004 |

(Continued)

OTHER PUBLICATIONS

Helmsworth, et al., "Molecular Surgery of the Basement Membrane by the Argon Laser," Lasers in Surgery and Medicine, 1990, pp. 576-583, vol. 10.
Hurst, et al., "Rehabilitation Following Microfracture for Chondral Injury in the Knee," Clin Sports Med., 2010, pp. 257-265, vol. 29.
Kurzweil, et al., "New Therapeutic Options for Managing the Arthritic Knee," A Supplement to the American Journal of Orthopedics, 2004, pp. 35-39, vol. 33, Supp. 2.
Steadman, et al., "Microfracture: Surgical Technique and Rehabilitation to Treat Chondral Defects," Clinical Orthopaedics and Related Research, 2001, pp. S362-S369, Supp. 391.
Steadman, et al., "Microfracture to Treat Full-Thickness Chondral Defects Surgical Technique, Rehabilitation, and Outcomes," The Journal of Knee Surgery, 2002, pp. 170-176, vol. 15, No. 3.
Vangsness, et al., "Restoring Articular Cartilage in the Knee," A Supplement to the American Journal of Orthopedics, 2004, pp. 29-34, vol. 33, Supp. 2.

(Continued)

*Primary Examiner* — Sreenivasan Padmanabhan
*Assistant Examiner* — Genevieve S Alley
(74) *Attorney, Agent, or Firm* — Polsinelli PC

(57) ABSTRACT

Compositions and methods for repair of tissue defects are disclosed. The compositions are prepared by entangling high molecular weight polycaprolactone polymer molecules with a polysaccharide such as hyaluronic acid by a dual solvent emulsion process to produce a porous flexible matrix which supports cell and tissue growth in vivo and ex vivo.

62 Claims, No Drawings

(56) References Cited

U.S. PATENT DOCUMENTS

| | | |
|---|---|---|
| 6,579,978 B1 | 6/2003 | Renier et al. |
| 6,596,274 B1 | 7/2003 | Abatangelo et al. |
| 6,626,950 B2 | 9/2003 | Brown et al. |
| 6,637,437 B1 | 10/2003 | Hungerford et al. |
| 6,662,805 B2 | 12/2003 | Frondoza et al. |
| 6,673,285 B2 | 1/2004 | Ma |
| 6,689,747 B2 | 2/2004 | Filvaroff et al. |
| 6,696,073 B2 | 2/2004 | Boyce et al. |
| 6,737,072 B1 | 5/2004 | Angele et al. |
| 6,852,330 B2 | 2/2005 | Bowman et al. |
| 6,886,568 B2 | 5/2005 | Frondoza et al. |
| 6,949,252 B2 | 9/2005 | Mizuno et al. |
| 7,087,745 B1 | 8/2006 | Pallado et al. |
| 7,316,822 B2 | 1/2008 | Binette et al. |
| 7,375,077 B2 | 5/2008 | Mao |
| 7,446,131 B1 | 11/2008 | Liu et al. |
| 7,824,711 B2 | 11/2010 | Kizer et al. |
| 8,192,759 B2 | 6/2012 | Seyedin et al. |
| 8,444,968 B2 | 5/2013 | Seyedin et al. |
| 8,512,730 B2 | 8/2013 | Seyedin et al. |
| 8,580,289 B2 | 11/2013 | Seyedin et al. |
| 2002/0004225 A1 | 1/2002 | Hart et al. |
| 2002/0009805 A1 | 1/2002 | Nevo et al. |
| 2002/0012705 A1 | 1/2002 | Domb |
| 2002/0028192 A1 | 3/2002 | Dimitrijevich et al. |
| 2002/0062151 A1 | 5/2002 | Altman et al. |
| 2002/0064559 A1 | 5/2002 | Lee et al. |
| 2002/0123142 A1 | 9/2002 | Hungerford et al. |
| 2002/0133235 A1 | 9/2002 | Hungerford et al. |
| 2002/0183858 A1 | 12/2002 | Contiliano et al. |
| 2003/0039695 A1 | 2/2003 | Geistlich et al. |
| 2003/0040113 A1 | 2/2003 | Mizuno et al. |
| 2003/0099620 A1 | 5/2003 | Zaleske et al. |
| 2004/0001879 A1 | 1/2004 | Guo et al. |
| 2004/0033212 A1 | 2/2004 | Thomson et al. |
| 2004/0048796 A1 | 3/2004 | Hariri et al. |
| 2004/0078073 A1 | 4/2004 | Bonutti |
| 2004/0078077 A1 | 4/2004 | Binette et al. |
| 2004/0078090 A1 | 4/2004 | Binette et al. |
| 2004/0117033 A1 | 6/2004 | Frondoza et al. |
| 2004/0126405 A1 | 7/2004 | Sahatjian et al. |
| 2004/0134502 A1 | 7/2004 | Mizuno et al. |
| 2004/0138664 A1 | 7/2004 | Bowman |
| 2004/0151705 A1 | 8/2004 | Mizuno et al. |
| 2004/0181240 A1 | 9/2004 | Tseng et al. |
| 2004/0191900 A1 | 9/2004 | Mizuno et al. |
| 2004/0219182 A1 | 11/2004 | Gomes et al. |
| 2004/0228901 A1 | 11/2004 | Trieu et al. |
| 2005/0038520 A1 | 2/2005 | Binette et al. |
| 2005/0043814 A1 | 2/2005 | Kusanagi et al. |
| 2005/0064042 A1 | 3/2005 | Vunjak-Novakovic et al. |
| 2005/0079202 A1 | 4/2005 | Chen et al. |
| 2005/0113937 A1 | 5/2005 | Binette et al. |
| 2005/0142163 A1 | 6/2005 | Hunter et al. |
| 2005/0152882 A1 | 7/2005 | Kizer et al. |
| 2005/0152949 A1* | 7/2005 | Hotchkiss ............ A61K 9/0024 424/423 |
| 2005/0177249 A1 | 8/2005 | Kladakis et al. |
| 2005/0186283 A1 | 8/2005 | Geistlich et al. |
| 2005/0186673 A1 | 8/2005 | Geistlich et al. |
| 2005/0196460 A1 | 9/2005 | Malinin |
| 2005/0222687 A1 | 10/2005 | Vunjak-Novakovic et al. |
| 2005/0226856 A1 | 10/2005 | Ahlfors |
| 2005/0251268 A1 | 11/2005 | Truncale |
| 2005/0288796 A1 | 12/2005 | Awad et al. |
| 2006/0002979 A1 | 1/2006 | Ashammakhi et al. |
| 2006/0008530 A1* | 1/2006 | Seyedin ............... A61K 31/727 424/486 |
| 2006/0019389 A1 | 1/2006 | Yayon et al. |
| 2006/0024826 A1 | 2/2006 | Bonassar et al. |
| 2006/0029679 A1 | 2/2006 | Dolecek |
| 2006/0111778 A1 | 5/2006 | Michalow |
| 2006/0128016 A1 | 6/2006 | Tokushima et al. |
| 2006/0140988 A1 | 6/2006 | Chen et al. |
| 2006/0147547 A1 | 7/2006 | Yayon |
| 2006/0153815 A1 | 7/2006 | Seyda et al. |
| 2006/0210643 A1 | 9/2006 | Truncale et al. |
| 2006/0216822 A1 | 9/2006 | Mizuno et al. |
| 2006/0228391 A1 | 10/2006 | Seyedin et al. |
| 2006/0251631 A1 | 11/2006 | Adkisson, IV et al. |
| 2007/0014867 A1 | 1/2007 | Kusanagi et al. |
| 2007/0031471 A1 | 2/2007 | Peyman |
| 2007/0038299 A1 | 2/2007 | Stone et al. |
| 2007/0041952 A1 | 2/2007 | Guilak et al. |
| 2007/0087032 A1 | 4/2007 | Chang et al. |
| 2007/0098759 A1 | 5/2007 | Malinin |
| 2007/0106394 A1 | 5/2007 | Chen |
| 2007/0128155 A1 | 6/2007 | Seyedin et al. |
| 2008/0009942 A1 | 1/2008 | Mizuno et al. |
| 2008/0039954 A1 | 2/2008 | Long et al. |
| 2008/0051624 A1 | 2/2008 | Bonutti |
| 2008/0065210 A1 | 3/2008 | McKay |
| 2008/0071385 A1 | 3/2008 | Binette et al. |
| 2008/0097605 A1 | 4/2008 | Pastorello et al. |
| 2008/0103564 A1 | 5/2008 | Burkinshaw et al. |
| 2008/0113007 A1 | 5/2008 | Kurihara et al. |
| 2008/0153157 A1 | 6/2008 | Yao et al. |
| 2008/0154370 A1 | 6/2008 | Mathies |
| 2008/0274157 A1 | 11/2008 | Vunjak-Novakovic et al. |
| 2009/0069901 A1 | 3/2009 | Truncale et al. |
| 2009/0143867 A1 | 6/2009 | Gage et al. |
| 2009/0149893 A1 | 6/2009 | Semler et al. |
| 2009/0155229 A1 | 6/2009 | Yayon |
| 2009/0181092 A1 | 7/2009 | Thorne et al. |
| 2009/0181093 A1 | 7/2009 | Thorne et al. |
| 2009/0181892 A1 | 7/2009 | Thorne et al. |
| 2009/0214614 A1 | 8/2009 | Everland et al. |
| 2009/0291112 A1 | 11/2009 | Truncale et al. |
| 2010/0036503 A1* | 2/2010 | Chen ................. A61L 27/3604 623/23.63 |
| 2010/0086594 A1 | 4/2010 | Amit et al. |
| 2010/0168856 A1 | 7/2010 | Long et al. |
| 2011/0009963 A1 | 1/2011 | Binnette et al. |
| 2011/0052705 A1 | 3/2011 | Malinin |
| 2011/0070271 A1 | 3/2011 | Truncale et al. |
| 2011/0086081 A1 | 4/2011 | To et al. |
| 2011/0091517 A1 | 4/2011 | Binette et al. |
| 2011/0097381 A1 | 4/2011 | Binette et al. |
| 2011/0196508 A1 | 8/2011 | Truncale et al. |
| 2011/0256095 A1 | 10/2011 | Seyedin et al. |
| 2012/0156265 A1 | 6/2012 | Binette et al. |
| 2013/0302401 A1* | 11/2013 | Ma ........................ A61L 31/10 424/450 |
| 2014/0142718 A1 | 5/2014 | Seyedin et al. |

FOREIGN PATENT DOCUMENTS

| | | |
|---|---|---|
| CA | 2445558 A1 | 4/2004 |
| CA | 2522133 A1 | 11/2004 |
| CA | 2475905 A1 | 2/2005 |
| CA | 2487029 A1 | 5/2005 |
| CA | 2496184 A1 | 8/2005 |
| CA | 2563082 A1 | 11/2005 |
| CA | 2261292 C | 9/2008 |
| EP | 0610423 B1 | 5/1997 |
| EP | 1538196 A1 | 6/2005 |
| EP | 1561481 A2 | 8/2005 |
| EP | 1410811 B1 | 10/2008 |
| GB | 2175507 A | 12/1986 |
| WO | 85/05274 A1 | 12/1985 |
| WO | 90/00060 A1 | 1/1990 |
| WO | 93/00050 A1 | 1/1993 |
| WO | 93/11803 A1 | 6/1993 |
| WO | 94/01468 A1 | 1/1994 |
| WO | 95/31157 A1 | 11/1995 |
| WO | 96/28539 A1 | 9/1996 |
| WO | 96/37165 A1 | 11/1996 |
| WO | 98/04681 A3 | 2/1998 |
| WO | 00/55300 A1 | 9/2000 |
| WO | 01/01895 A1 | 1/2001 |
| WO | 01/35968 A1 | 5/2001 |
| WO | 02/072662 A1 | 9/2002 |
| WO | 02/076335 A2 | 10/2002 |
| WO | 03/039615 A2 | 5/2003 |

(56) References Cited

FOREIGN PATENT DOCUMENTS

| | | |
|---|---|---|
| WO | 03/077794 A2 | 9/2003 |
| WO | 2004/028584 A1 | 4/2004 |
| WO | 2005/060987 A1 | 7/2005 |
| WO | 2005/061018 A1 | 7/2005 |
| WO | 2006/033698 A2 | 3/2006 |
| WO | 2006/058221 A2 | 6/2006 |
| WO | 2006/068972 A2 | 6/2006 |
| WO | 2006/071694 A1 | 7/2006 |
| WO | 2006/113642 A1 | 10/2006 |
| WO | 2007/067637 A2 | 6/2007 |
| WO | 2007/102149 A2 | 9/2007 |
| WO | 2007143726 A2 | 12/2007 |
| WO | 2009/108934 A2 | 9/2009 |
| WO | 2014/078792 A1 | 5/2014 |

OTHER PUBLICATIONS

International Search Report and Written Opinion regarding PCT/US2013/070573 dated Mar. 19, 2014, 9 pages.
International Search Report and Written Opinion relating to International Application No. PCT/US07/70631, dated Sep. 16, 2008, 10 pgs.
International Search Report and Written Opinion relating to International Application No. PCT/US2006/046576, dated Oct. 22, 2008, 8 pgs.
Jalil et al., "Biodegradable poly(lactic acid) and poly(lactide-co-glycolide) microcapsules: problems associated with preparative techniques and release properties", J. Microencapsulation, 1990, pp. 297-325, vol. 7, No. 3.
Jeong et al., "Three-dimensional polycaprolactone scaffold-conjugated bone morphogenetic protein-2 promotes cartilage regeneration from primary chondrocytes in vitro and in vivo without accelerated endochondral ossification", Journal of Biomedical Materials Research Part A, 2012, pp. 2088-2096, vol. 100A, No. 8.
Jin et al., "Human Amniotic Membrane as a Delivery Matrix for Articular Cartilage Repair", Tissue Engineering, 2007, pp. 693-703, vol. 13, No. 4.
Kim et al., "Synthesis and Characterization of Injectable Poly(N-isopropylacrylamide-co-acrylic acid) Hydrogels with Proteolytically Degradable Cross-Links", Biomacromolecules, 2003, pp. 1214-1223, vol. 4, No. 5.
Kon et al., "Second Generation Issues in Cartilage Repair", Sports Med Arthrosc Rev., 2008, pp. 221-229, vol. 16, No. 4.
Kranz et al. "Physicomechanical Properties of Biodegradable Poly(D,L-lactide) and Poly(D,L-lactide-co-glycolide) Films in the Dry and Wet States", Journal of Pharmaceutical Sciences, 2000, pp. 1558-1566, vol. 89, No. 12.
Kuettner, "Biochemistry of Articular Cartilage in Health and Disease", Clinical Biochemistry, 1992, pp. 155-163, vol. 25.
Kuo et al., "Chemical Modification of Hyaluronic Acid by Carbodiimides", Bioconjugate Chem., 1991, pp. 232-241, vol. 2, No. 4.
Libera et al., Cartilage Engineering, Fundamentals of Tissue Engineering and Regenerative Medicine, 2009, pp. 233-242, Chapter 18, Springer-Verlag, Berlin Heidelberg.
Marmotti et al., "One-step osteochondral repair with cartilage fragments in a composite scaffold", Knee Surg Sports Traumatol Arthrosc, 2012, 12 pgs.
Mason et al., "Attachment of hyaluronic acid to polypropylene, polystyrene, and polytetrafluoroethylene", Biomaterials, 2000, pp. 31-36, vol. 21.
Minas et al., "Current Concepts in the Treatment of Articular Cartilage Defects", Orthopedics, 1997, pp. 525-538, vol. 20, No. 6.
Nehrer et al., "Three-year clinical outcome after chondrocyte transplantation using a hyaluronan matrix for cartilage repair", European Journal of Radiology, 2006, pp. 3-8, vol. 57, No. 1.
Obradovic et al., "Integration of engineered cartilage", Journal of Orthopaedic Research, 2001, pp. 1089-1097, vol. 19, No. 6.

Oh et al., "In vitro and in vivo characteristics of PCL scaffolds with pore size gradient fabricated by a centrifugation method", Biomaterials, 2007, pp. 1664-1671, vol. 28.
Peretti et al., "Bonding of Cartilage Matrices with Cultured Chondrocytes: An Experimental Model", Journal of Orthopaedic Research, 1998, pp. 89-95, vol. 16.
Peretti et al., "Cell-Based Tissue-Engineered Allogeneic Implant for Cartilage Repair", Tissue Engineering, 2000, pp. 567-576, vol. 6, No. 5.
Peretti et al., "A Biomechanical Analysis of an Engineered Cell-Scaffold Implant for Cartilage Repair", Annals of Plastic Surgery, 2001, pp. 533-537, vol. 46, No. 5.
Peretti et al., "In vitro bonding of pre-seeded chondrocytes", Sport Sci Health, 2007, pp. 29-33, vol. 2.
Robinson et al., "Regenerating Hyaline Cartilage in Articular Defects of Old Chickens Using Implants of Embryonal Chick Chondrocytes Embedded in a New Natural Delivery Substance", Calcified Tissue International, 1990, pp. 246-253, vol. 46, No. 4.
Sampath et al., "In vitro transformation of mesenchymal cells derived from embryonic muscle into cartilage in response to extracellular matrix components of bone", PNAS, 1984, pp. 3419-3423, vol. 81, No. 11.
Sannino et al., "Biodegradable Cellulose-based Hydrogels: Design and Applications", Materials, 2009, pp. 353-373, vol. 2.
Sarasam et al., "Blending Chitosan with Polycaprolactone: Porous Scaffolds and Toxicity", Macromolecular Bioscience, 2007, pp. 1160-1167, vol. 7.
Schagemann et al., "The effect of scaffold composition on the early structural characteristics of chondrocytes and expression of adhesion molecules", Biomaterials, 2010, pp. 2798-2805, vol. 31.
Schreiber et al., "A Method for Tissue Engineering of Cartilage by Cell Seeding on Bioresorbable Scaffolds", Annals New York Academy of Sciences, 1999, pp. 398-404, vol. 875.
Schwarz et al., "The Influence of Fibrin Sealant on Demineralized Bone Matrix-Dependent Osteoinduction", Clinical Orthopaedics and Related Research, 1989, pp. 282-287, No. 238.
Seliktar, "Nature's Healing Matrix", Lecture Bulletin, Technion Focus, May 2006, 1 page.
Sierra et al., "Fibrin-Collagen Adhesive Drug Delivery System for Tumor Therapy", Trans. Soc. Biomater., 1993, p. 257, vol. 16.
Stone et al., "New Techniques for Cartilage Repair and Replacement", Knee Ligament Rehabilitation, Ellenbecker T.S., Jun. 2000, 11 pgs.
Uematsu et al., "Cartilage regeneration using mesenchymal stem cells and a three-dimensional poly-lactic-glycolic acid (PLGA) scaffold", Biomaterials, 2005, pp. 4273-4279, vol. 26, No. 20.
Wakitani et al., "Repair of Rabbit Articular Surfaces with Allograft Chondrocytes Embedded in Collagen Gel", The Journal of Bone and Joint Surgery, 1989, pp. 74-80, vol. 71-B, No. 1.
Wang et al., "Morphological development in absorbable poly(glycolide), poly(glycolide-co-lactide) and poly(glycolide-co-caprolactone) copolymers during isothermal crystallization", Polymer, 2000, pp. 621-628, vol. 41.
Zhang et al., "Preparation of Hydroxyapatite / Poly($\epsilon$-caprolactone) Hybrid Microspheres for Drug Release System", Key Engineering Materials, 2007, pp. 1045-1048, vols. 330-332.
Zhao et al., "Synthesis and characterization of a novel double crosslinked hyaluronan hydrogel", Journal of Materials Science: Materials in Medicine, 2002, pp. 11-16, vol. 13.
Amiel et al., "Rib Perichondrial Grafts for the Repair of Full-Thickness Articular-Cartilage Defects", The Journal of Bone and Joint Surgery, 1985, pp. 911-920, vol. 67k.
Armentano et al., "Biodegradable polymer matrix nanocomposites for tissue engineering: A review", Polymer Degradation and Stability, 2010, pp. 2126-2146, vol. 95.
Benesova et al., "Stability Evaluation of n-Alkyl Hyaluronic Acid Derivatives by DSC and TG Measurement", Journal of Thermal Analysis and Calorimetry, 2006, pp. 341-348, vol. 83, No. 2.
Benjamin et al., "Biology of Fibrocartilage Cells", International Review of Cytology, 2004, pp. 1-45, vol. 233.
Blein-Sella et al., "Rabbit Articular Chondrocyte Functional Toxicity Test", Methods in Molecular Biology, 1995, Chapter 19, pp. 169-175, vol. 43.

(56) References Cited

OTHER PUBLICATIONS

Cheng et al., "Chondrogenic Differentiation of Adipose-Derived Adult Stem Cells by a Porous Scaffold Derived from Native Articular Cartilage Extracellular Matrix", Tissue Engineering: Part A, 2009, pp. 231-241, vol. 15, No. 2.

Ciardelli et al., "Blends of Poly-(ε-caprolactone) and Polysaccharides in Tissue Engineering Applications", Biomacromolecules, 2005, pp. 1961-1976, vol. 6, No. 4.

De Gennes, "Reptation of a Polymer Chain in the Presence of Fixed Obstacles", The Journal of Chemical Physics, 1971, pp. 572-579, vol. 55, No. 2.

Dietz et al., "Alterations of Collagen mRNA Expression During Retinoic Acid Induced Chondrocyte Modulation: Absence of Untranslated α1(I) mRNA in Hyaline Chondrocytes", Journal of Cellular Biochemistry, 1993, pp. 57-68, vol. 52.

Edwards, "The statistical mechanics of polymerized material", Proc. Phys. Soc., 1967, pp. 9-16, vol. 92.

Ekaputra et al., "The three-dimensional vascularization of growth factor-releasing hybrid scaffold of poly(ε-caprolactone)/collagen fibers and hyaluronic acid hydrogel", Biomaterials, 2011, pp. 8108-8117, vol. 32.

European Search Report from related European Application No. 06839104.4, dated Oct. 28, 2009, 6 pgs.

European Search Report from related European Application No. 13855076.9, dated Aug. 11, 2016, 9 pgs.

European Search Report from related European Application No. 05812025.4, dated Jul. 29, 2011, 6 pgs.

Fu et al., "Autologous Chondrocyte Implantation Versus Debridement for Treatment of Full-Thickness Chondral Defects of the Knee—An Observational Cohort Study With 3-Year Follow-up", The American Journal of Sports Medicine, 2005, pp. 1658-1666, vol. 33, No. 11.

Fukuzaki et al., "In vivo characteristics of low molecular weight copolymers composed of L-lactic acid and various DL-hydroxy acids as biodegradable carriers for drug delivery systems", Biomaterials, 1990, pp. 441-446, vol. 11.

Gilbert, "Current Treatment Options for the Restoration of Articular Cartilage", The American Journal of Knee Surgery, 1998, pp. 42-46, vol. 11, No. 1.

Gombotz et al., "Biodegradable Polymers for Protein and Peptide Drug Delivery", Bioconjugate Chem., 1995, pp. 332-351, vol. 6, No. 4.

Gross, "Cartilage Resurfacing—Filling Defects", The Journal of Arthroplasty, 2003, pp. 14-17, vol. 18, No. 3.

Hoekstra, "Hyaluronan-Modified Surfaces for Medical Devices", www.devicelink.com/grabber.php3?URL=http://www.devicelink.com/mddi/archive, Medical Device & Diagnostic Industry Magazine, 1999, print date Oct. 14, 2005, 15 pgs.

Hollinger, "Preliminary report on the osteogenic potential of a biodegradable copolymer of polyactide (PLA) and polyglycolide (PGA)", Journal of Biomedical Materials Research, 1983, pp. 71-82, vol. 17.

Hunziker, "Articular cartilage repair: basic science and clinical progress. A review of the current status and prospects", Osteoarthritis and Cartilage, 2001, pp. 432-463, No. 10, No. 6.

\* cited by examiner

FLEXIBLE TISSUE MATRIX AND METHODS FOR JOINT REPAIR

TECHNICAL FIELD

The present disclosure relates to compositions and methods for tissue repair including repair of defects in bone and/or cartilage tissue.

BACKGROUND

Defects of articular joints are significant sources of pain, discomfort and disability. These defects, such as full-thickness chondral defects, may be associated with osteoarthritis or other disease, traumatic injury and/or age or use-related degeneration of articular cartilage. Morbidity associated with defects of hyaline cartilage comprised by articular joints is responsible for significant economic, health and social costs.

The success of a tissue graft, for example a bone graft, in tissue repair is determined by its ability to recruit host cells to the site of the graft and modulate their conversion into the appropriate replacement tissue to repair the defect. For example, a bone graft relies on the ability of the graft to recruit osteoblasts and other bone-forming cells. This will depend on the osteoconductive, osteoinductive and osteogenic capabilities of the graft. Currently, autograft bone harvested from the iliac crest is considered the 'gold standard' due to its superior osteogenic properties. However, associated donor site morbidity, an increased surgery and recovery time, and a limited supply of donor bone are limiting its use. Allograft bone is a logical alternative to autograft. However, it must be rigorously processed and terminally sterilized prior to implantation to remove the risk of disease transmission or an immunological response. This processing removes the osteogenic and osteoinductive properties of the graft, leaving only an osteoconductive scaffold.

Current treatments for repair or amelioration of joint problems also include microfracture, abrasion and drilling to expose a joint containing a defect to mesenchymal stem cells. As a result of such interventions, the mesenchymal stem cells can infiltrate the defect, and differentiate into fibrocartilage over time. However, fibrocartilage has a structure and molecular composition distinct from that of the hyaline cartilage found in joints. The resulting fibrocartilage generally provides only short-term improvement, typically lasting less than two years. Alternative treatments are therefore needed.

BRIEF SUMMARY OF THE INVENTION

In one aspect, the present disclosure provides a composition for supporting repair of biological tissues comprising high molecular weight caprolactone polymer molecules entangled with polysaccharide polymer molecules by a dual solvent emulsion process to form a flexible matrix, and at least one biologically active agent. In any of the compositions, the at least one biologically active agent can comprise for example an agent selected from: demineralized bone matrix (DBM), DBM cortical powder, crushed bone such as crushed cancellous bone, platelets, platelet lysate, platelet rich plasma, bone marrow aspirate, cells including chondrogenic cells, a growth factor, and bioglass, or any combination thereof. Any biologically active agent derived from bone can be derived for example from allogenic bone.

In any of the disclosed compositions, the biologically active agent can comprise cells. For example, the cells can be chondrogenic cells, including for example adult neuronal stem cells, chondrocytes, notochordal cells, mesenchymal stem cells, and induced pluripotent stem cells. The biologically active agent can comprise any cells derived from a body tissue, for example mesenchymal stem cells derived from a source selected from the group consisting of: bone marrow, adipose tissue, synovium, periosteum, post-partum connective tissue, placenta, cord blood, and umbilical cord.

In any of the disclosed compositions, the high molecular weight caprolactone polymer molecules in the composition may be selected from polycaprolactone; a co-polymer of polylactic acid and polycaprolactone; a co-polymer of polyglycolic acid and polycaprolactone; a copolymer of polylactic acid, polyglycolic acid, and polycaprolactone; a co-polymer of polyethylene glycol, polylactic acid and polycaprolactone; a co-polymer of polyethylene glycol, polyglycolic acid and polycaprolactone; and a copolymer of polyethylene glycol, polylactic acid, polyglycolic acid, and polycaprolactone.

The high molecular weight caprolactone polymers in any composition can comprise the copolymer poly (L-lactide-co-caprolactone) (PLCL). The PLCL polymers can comprise, in non-limiting example, a 70:30 (w/w) ratio of L-lactide to caprolactone polymers. In another non-limiting example, the composition comprises PLCL, such as but not limited to PLCL (70:30), and the polysaccharide polymer molecules comprise HA. In another non-limiting example, the composition comprises PLCL, such as but not limited to PLCL (70:30), and the polysaccharide polymer molecules comprise PLGA. The PLGA can comprise for example, a 75:25 (w/w) ratio of poly-lactic acid polymers to polyglycolic acid polymers. In one example, the composition comprises PLCL and PLGA combined at a w/w ratio of about 1:1, 1:2,1:3, 2:1, 2:3, 3:1, or 3:2, or at any w/w ratio of about 1:3 to about 3:2. In one example, the composition comprises PLCL (70:30), and PLGA (75:25), combined at a w/w ratio of about 1:1, 1:2,1:3, 2:1, 2:3, 3:1, or 3:2, or at any w/w ratio of about 1:3 to about 3:2.

In any of the disclosed compositions, the polysaccharide polymer molecules can be derived from a bacterial source or chemically synthesized, and/or can comprise sulfated or non-sulfated polysaccharide polymer molecules or any combination thereof. The polysaccharide polymer molecules can be oxidized, and/or covalently cross-linked, or otherwise modified or derivatized. In any of the disclosed compositions, the polysaccharide polymer molecules can comprise for example cellulose, inulin, starch, heparin, and/or one or more glycosaminoglycans (GAGs), such as but not limited to chitin, hyaluronic acid (HA), chondroitin, dermatan, chondroitin/dermatan, keratan, heparan, heparan, dextran, alginate, or any combination thereof. Any polysaccharide polymer molecules used in the composition can be sulfated or non-sulfated polysaccharide polymer molecules, or can be a combination thereof. Sulfated polysaccharides that can be used for the polysaccharide polymer molecules include, for example, chondroitin sulfate, dermatan sulfate, keratan sulfate, heparan sulfate, and dextran sulfate, or any combination thereof, or any combination of any of the foregoing sulfated polysaccharides with any non-sulfated polysaccharide.

In any of the compositions described herein, unless indicated otherwise, the polysaccharide polymer molecules can comprise hyaluronic acid (HA) polymer molecules. HA polymer molecules can comprise for example about 5% to about 20% by weight of the composition, preferably about 8% to about 12% by weight of the composition. The high molecular weight caprolactone polymer molecules and the hyaluronic acid polymers can be combined for example in the composition such that the weight (w/w) ratio is from about 99:1 to about 1:99 (high molecular weight caprolactone polymer molecules to HA polymer molecules).

In any of the compositions described herein, the at least one biologically active agent can comprise at least one growth factor. The at least one growth factor can be for example an isolated growth factor previously isolated from bone, including allogenic bone, such as in non-limiting example a bone morphogenetic protein. Non-limiting examples of growth factors that can be used in the biologically active agent are basic fibroblast growth factor (bFGF), FGF2, FGF-18, transforming growth factor (TGF-β), BMP-2, BMP-4, BMP-7, ADMP-1, PDGF-bb, EGF, Pleotrophin, SDF-1, a hedgehog protein, an insulin-like growth factor, a platelet-derived growth factor, an interleukin, a colony-stimulating factor, and an activin. The biologically active agent can comprise a collagen such as a type I collagen or a type II collagen, or any combination thereof.

Any of the compositions described herein can be characterized by a flexibility exhibited when composition is at about room temperature, i.e., at least above or about 20° C., and maintains the room temperature flexibility when cooled to a temperature of less than about 20° C. For example, compositions disclosed herein can maintains the room temperature flexibility when cooled to a temperature of about 0° C. to about 15° C.

Any tissue matrix composition disclosed herein may further include molecules of a second polymer, such as a polyester polymer, which are not copolymerized with the high molecular weight caprolactone polymer, yet are entangled with the high molecular weight caprolactone polymer molecules and the polysaccharide polymer molecules by the dual solvent emulsion process. Such a second polymer (not copolymerized with the high molecular weight caprolactone polymer molecules) can comprise at least one of: polylactic acid (PLA), polyglycolic acid (PGA), or a copolymer of polylactic acid and polyglycolic acid (PLGA). For example, compositions disclosed herein encompass a composition comprising a copolymer of polyglycolic acid and polycaprolactone as the high molecular weight polycaprolactone polymers, and further comprising polylactic acid not copolymerized but entangled with the copolymer of polyglycolic acid and polycaprolactone via the dual solvent emulsion process. When a composition as disclosed herein includes such a second polymer, the combined weight of the second polymer with the weight of the high molecular weight polycaprolactone polymer provide a total polymer weight, wherein the weight ratio of the total polymer weight to the hyaluronic acid polymer weight is from about 99:1 to 1:99, preferably from about 9:1 to about 1:9, and more preferably from about 3:1 to about 7:3. A composition may include, for example, the polylactic acid and the copolymer of polyglycolic acid and polycaprolactone in the composition in a w/w ratio of from about 9:1 to about 1:9. Preferably, a composition includes the polylactic acid and the copolymer of polyglycolic acid and polycaprolactone in the composition in a w/w ratio of from about 3:1 to about 7:3.

Any of the compositions described herein can further comprise at least one flexibility agent. A flexibility agent can be added to the composition at a weight (w/w) ratio, relative to the high molecular weight caprolactone polymer molecules, of about 9:1 to 99:1, and any weight ratio within that range (high molecular weight caprolactone polymer molecules to flexibility agent (w/w)). For example, any composition as disclosed above comprising polylactic acid and the copolymer of polyglycolic acid and polycaprolactone can be combined with a flexibility agent, such that the ratio of a total polymer weight of the polylactic acid and the copolymer of polyglycolic acid and polycaprolactone combined to the flexibility agent is from about 9:1 to about 99:1. The flexibility agent can be selected from triethyl citrate, acetyl tributyl citrate, acetyl triethyl citrate, tributyl citrate, trimethyl citrate, trihexyl citrate, acetyl trihexyl citrate, trioctyl citrate, acetyl trioctyl citrate and any combination thereof. Alternatively, the flexibility agent can be polyethylene glycol, polyethylene glycol monoalkyl ether, propylene glycol, glycerin, triacetin and any combination thereof.

For example, compositions disclosed herein encompass a composition comprising a copolymer of polyglycolic acid and polycaprolactone as the high molecular weight polycaprolactone polymers, HA polymer molecules as the polysaccharide polymer molecules, and further comprising polylactic acid not copolymerized but entangled with the copolymer of polyglycolic acid and polycaprolactone via the dual solvent emulsion process. Such a composition may include, for example, the polylactic acid and the copolymer of polyglycolic acid and polycaprolactone in the composition in a w/w ratio of from about 9:1 to about 1:9. Preferably, a composition includes the polylactic acid and the copolymer of polyglycolic acid and polycaprolactone in the composition in a w/w ratio of from about 3:1 to about 7:3. In such a composition, the HA polymer molecules can comprise about 5% to about 20% by weight of the composition, and preferably about 8% to about 12% by weight of the composition. In such a composition, the HA polymer molecules have a total HA weight, and the polyester polymer molecules not copolymerized with the high molecular weight polycaprolactone polymer molecules, together with the high molecular weight polycaprolactone polymer molecules have a total polyester weight, and the composition can be prepared such that the ratio of the total polyester weight to the total HA weight in the composition is from about 99:1 to about 1:99, for example from about 5:1 to about 10:1.

In any of the foregoing compositions comprising PLA for the polyester molecules, PLGA can be substituted for the PLA, in whole or part, for the polyester polymer molecules. In any of the foregoing compositions, the high molecular weight caprolactone polymers can comprise poly (L-lactide-co-caprolactone) (PLCL). PLGA can be for example PLGA 75:25 (polylactic acid:polyglycolic acid), and the PLCL can be for example 70:30 (poly-L-lactide:caprolactone). When PLGA and PLCL are combined in a composition as disclosed herein, they may be combined for example at any w/w ratio of about 1:1, 1:2,1:3, 2:1, 2:3, 3:1, or 3:2. Preferably the PLGA and PLCL are combined at a w/w ratio of about 1:3 to about 3:2, 2:1 to about 3:1, or 3:2 to about 3:1.

A composition as disclosed herein can include high molecular weight caprolactone polymer molecules entangled with the polysaccharide polymers to form a polymer matrix having a gel temperature below about 20° C. Such compositions also encompass those in which the high molecular weight caprolactone polymer molecules are selected from polycaprolactone; a co-polymer of polylactic acid and polycaprolactone; a co-polymer of polyglycolic acid and polycaprolactone; a copolymer of polylactic acid, polyglycolic acid, and polycaprolactone; a co-polymer of polyethylene glycol, polylactic acid and polycaprolactone; a co-polymer of polyethylene glycol, polyglycolic acid and polycaprolactone; and a copolymer of polyethylene glycol, polylactic acid, polyglycolic acid, and polycaprolactone; and preferably a co-polymer selected from a copolymer of polylactic acid and polycaprolactone; a co-polymer of polyglycolic acid and polycaprolactone; a copolymer of polylactic acid, polyglycolic acid and polycaprolactone; a co-polymer of polyethylene glycol, polylactic acid and polycaprolactone; a co-polymer of polyethylene glycol, polyglycolic acid and polycaprolactone; and a copolymer of polyethylene glycol, polylactic acid, polyglycolic acid, and polycaprolactone. Any such composition can also further comprise at least one flexibility agent as described above, at a w/w ratio of the high molecular weight caprolactone polymer molecules to the flexibility agent as also disclosed above.

Any of the compositions disclosed herein can be characterized by the ability to promote growth of cells in vivo or ex vivo when contacted with cells in vivo or ex vivo. Any of the compositions disclosed herein can be characterized as a porous matrix having pores of a structure and shape when dry, and further characterized by (i) retention of the same pore structure and shape when hydrated and (ii) the ability to support the growth of cells in vivo or ex vivo when contacted with cells in vivo or ex vivo.

Any of the compositions disclosed herein has a flexibility at about room temperature and maintains the room temperature flexibility when cooled to a temperature below about 20° C., and for example can maintain the room temperature flexibility when cooled to any temperature below about 20° C., or to any temperature within a range below about 20° C., for example from about 0° C. to about 15° C.

Any of the compositions disclosed herein can be formed as a membrane. For example, a membrane comprising any of the disclosed compositions can have a thickness of at least about 0.5 mm up to about 3 mm. Such a membrane can have a flexibility at about room temperature and can maintain the room temperature flexibility when cooled to a temperature of less than about 20° C., and for example can maintain the room temperature flexibility when cooled to any temperature below about 20° C., or to any temperature within a range below about 20° C., for example from about 0° C. to about 15° C. Such a membrane can further have a compressive resistance and a conformability at room temperature, wherein the membrane maintains the room temperature compressive resistance and conformability when cooled to a temperature of less than about 20° C., and for example can maintain the room temperature flexibility when cooled to any temperature below about 20° C., or to any temperature within a range below about 20° C., for example from about 0° C. to about 15° C.

In another aspect, the present disclosure provides a method for repairing a tissue defect in a subject in need thereof, the method comprising applying to the tissue defect any of the compositions or membranes disclosed herein. The subject can be a human or a non-human mammal. The tissue defect can be any tissue defect susceptible to treatment using the disclosed compositions and membranes. The tissue defect can be for example a bone defect or a cartilage defect, or a combination thereof. The tissue defect can comprise at least one of a bone defect and a cartilage defect. The tissue defect can be in a joint of the subject, such as for example in an ankle, knee, hip, sacroiliac joint, elbow, wrist, shoulder, jaw (temporomandibular), knuckle, interphalangeal joint, and atlanto-occipital joint, atlanto-axial joint, and intervertebral joint. For example, the method can be applied to the repair of hyaline cartilage in a mammal, or the repair of any joint in a mammal having a combined bone and cartilage defect. A method for repairing a bone and/or cartilage defect in a joint in a mammal using the compositions described herein can comprise, for example, infiltrating the joint with autologous mesenchymal stem cells; and applying to the joint a membrane as disclosed herein. Infiltrating the joint with autologous mesenchymal stem cells may involve for example introducing at least one aperture into the bone underlying the joint, wherein the at least one aperture is sufficiently large to allow migration of the autologous bone mesenchymal stem cells from the bone marrow cavity to the joint. Introducing an aperture into bone underlying the joint may involve, for example, abrading, microfracturing or drilling the bone underlying the hyaline cartilage defect. The bone or cartilage defect may comprise a full-thickness chondral defect. Applying the membrane to the joint may precede infiltrating the joint with autologous mesenchymal stem cells or alternatively, infiltrating the joint with autologous mesenchymal stem cells may precede applying the membrane to the joint. The method may further include securing the membrane to the joint, for example by attaching at least one fastener to the membrane and the joint. A fastener may be a biocompatible glue such as a fibrin glue, a suture, a tissue weld, a dart, a staple, a screw, or a tack. The method may further include applying to the joint a DBM composition, crushed bone and/or allogenic bone.

In another aspect the present disclosure provides a method for repairing a full-thickness chondral defect in a joint of a patient in need of such repair, the method comprising: microfracturing bone underlying the joint; applying to the joint a membrane comprising a tissue matrix comprising a high molecular weight caprolactone polymer entangled with a polysaccharide, wherein the membrane has a thickness of at least about 0.5 mm up to about 3 mm; and anchoring the membrane to the joint. The joint may be for example a knee joint.

In another aspect, the present disclosure provides a composition for supporting repair of a tissue defect in a subject, comprising: high molecular weight caprolactone polymer molecules comprising PLCL molecules, hyaluronic acid (HA) polymer molecules and PLGA molecules, wherein the PLGA molecules are not copolymerized with the high molecular weight polycaprolactone polymer molecules, and wherein the PLCL, HA and PLGA molecules are entangled together by a dual solvent emulsion process and combined with at least one biologically active agent to form a flexible matrix, wherein the flexible matrix has a flexibility at a room temperature, wherein the room temperature flexibility is maintained when the flexible matrix is cooled to a temperature of less than about 20° C. In such a composition, the HA polymer molecules can have a total HA weight, and he polyester polymer molecules not copolymerized with the high molecular weight polycaprolactone polymer molecules, together with the high molecular weight polycaprolactone polymer molecules can have a total polyester weight, and the composition can be prepared such that the ratio of the total polyester weight to the total HA weight in the composition is from about 99:1 to about 1:99. The HA polymer molecules can comprise about 5% to about 20% by weight of the composition, and preferably about 8% to about 12% by weight of the composition.

DETAILED DESCRIPTION

The present disclosure provides a composition for supporting repair of biological tissues comprising: high molecular weight caprolactone polymer molecules entangled with polysaccharide polymer molecules by a dual solvent emulsion process to form a flexible matrix, and at least one biologically active agent. A composition can optionally further comprise molecules of an additional polymer, e.g. a polyester polymer, not copolymerized with the high molecular weight caprolactone polymer molecules, but entangled with the high molecular weight caprolactone polymer molecules and the polysaccharide polymer molecules by the dual solvent emulsion process. Compositions disclosed herein can optionally include one or more small molecule flexibility agents.

Surprisingly, the high molecular weight polycaprolactone polymer molecules, when entangled with polysaccharide molecules through the dual solvent emulsion process, form matrices with advantages relative to matrices prepared without benefit of the high molecular weight polycaprolactone polymer molecules. Among such advantages are: 1) increased flexibility at temperatures usually encountered in operating theater (e.g., below about 20° C.), while retaining the compressive resistant nature of the matrix; 2) increased aqueous absorption at physiological temperatures while maintaining a good dissolution profile relevant to the time scales for tissue regeneration; and 3) reductions in the appearance of a shiny surface on strips formed or made from the composition, as is the result with other matrices not including the high molecular weight polycaprolactone polymer molecules. This last effect is believed to be the result of migration of the polysaccharide in the composition away from the exposed surface of the strips during the manufacturing process.

The observed advantages of the disclosed compositions, including retention of flexibility at cooler temperatures, avoid or reduce the need to further treat or manipulate the composition as it is being used in the surgical environment, which is usually cooled below room temperature. In contrast, a tissue matrix using only PLA, PGA or PLGA polymers is relatively brittle under typical surgical conditions, and thus requires some form of additional heating to facilitate its use. Without being bound by theory, it is believed that the increased absorbency of the improved tissue matrices described herein may be related to an improved ability for these matrices to imbibe and attach cellular component and further tissue formation.

The flexible tissue matrix can be used in methods for repairing a full-thickness chondral defect in a joint of a patient in need of treatment. Defects which may be treated may be any form of joint defect involving loss of or damage to hyaline cartilage, such as, but not limited to, a full-thickness defect, a partial-thickness defect, an age-related degenerative disease defect such as osteoarthritis, a congenital defect, or an injury resulting from trauma. In particular, such methods may include contacting the joint with, or introducing into the joint, cells which may differentiate into chondrocytes, such as mesenchymal stem cells, and applying to the joint a membrane comprising a flexible tissue matrix as described herein. Contact between the damaged joint and autologous mesenchymal stem cells from the underlying bone may be achieved for example using a microfracture technique as described in further detail below.

A. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "mesenchymal stem cells" refers to pluripotent cells which originate within juvenile or adult mesenchymal tissue. Autologous mesenchymal stem cells may be autologous bone mesenchymal stem cells, i.e., autologous mesenchymal stem cells which originate within the marrow cavity of a bone.

As used interchangeably herein, the terms "demineralized bone matrix" and "DBM" refer to allograft bone tissue with the inorganic mineral removed, leaving organic collagen including biologically active bone morphogenetic proteins.

The terms "hyaluronic acid", "hyaluronate" and "HyA" are used interchangeably herein to refer to the free acid form of hyaluronic acid, a salt of hyaluronic acid such as sodium hyaluronate, or a combination thereof.

B. Flexible Tissue Matrix

A tissue matrix composed of a polyester entangled with a polysaccharide, and methods of entangling a polyester and a polymer using a dual solvent emulsion process, are described in U.S. Pat. No. 8,192,759, "Tissue Matrix System and in Pat. Pub. No. U.S. 2014/0142718 A1 (U.S. patent application Ser. No. 13/837,849), the entire disclosures of which are herein incorporated by reference.

"Entanglement" and related terms, as used herein, refers to a state of polymers in melts or concentrated solutions above the overlap concentration, in which individual polymer molecules interpenetrate one another and motion of the molecules is restricted to movement along a virtual tube which surrounds each molecule. (See, e.g., Glossary of Colloid and Polymer Science. When entangled in this way, the resulting polymer matrix has a structure that is distinguished from other structures which can be formed by polymers, such as interpenetrating polymer networks in which at least two discrete polymer networks are combined in such a way that at least portions of each polymer network interlace with one another. Entanglement as described herein does not result from simple mixture of two or more polymers; creation of an interpenetrating polymer network ("IPN", or polymer blend); or creation of a polymer network, heteropolymer or copolymer out of more than one kind of monomer simply bonded to each other to form the network.

The present disclosure provides improved compositions formed from the entanglement of polymers as described herein, for supporting tissue repair. The compositions comprise high molecular weight polycaprolactone polymer molecules entangled at least with polysaccharide molecules, and optionally further entangled with polyester polymer molecules not copolymerized with the high molecular weight polymer molecules. The compositions disclosed herein also include one or more biologically active agents, such as but not limited to demineralized bone matrix (DBM), DBM cortical powder, crushed cancellous bone, platelets, platelet lysate, platelet rich plasma, bone marrow aspirate, chondrogenic cells. bioglass, a growth factor, a collagen such as a type I collagen or a type II collagen, or any combination thereof.

In any of the disclosed compositions, the high molecular weight polycaprolactone polymer molecules can be molecules of a caprolactone polymer such as polycaprolactone (PCL); a co-polymer of polylactic acid (PLA) and polycaprolactone (poly(lactide-co-caprolactone) (PLCL); a co-polymer of polyglycolic acid (PGA) and caprolactone (poly (glycolide-co-caprolactone) (PGCL); a copolymer of polycaprolactone and both polylactic acid and polyglycolic acid (e.g., PGA-PLCL, PLA-PGCL); a co-polymer of polyethylene glycol (PEG), polylactic acid and polycaprolactone (e.g., PEG-PLCL, PLA-PEG-PCL and PLA-PEG-PLCL); a co-polymer of polyethylene glycol, polyglycolic acid and polycaprolactone (e.g., PEG-PGCL, PGA-PEG-PCL and PGA-PEG-PGCL); or a copolymer of polyethylene glycol, polylactic acid, polyglycolic acid, and polycaprolactone (e.g., PLA-PEG-PGCL, PGA-PEG-PLCL, PLA-PEG-PGA-PCL; PGA-PEG-PLA-PCL).

Any of these high molecular weight polycaprolactone polymers may further be combined with a second polymer selected from polyester molecules such as polylactic acid (PLA), polyglycolic acid (PGA), or a copolymer of polylactic acid and polyglycolic acid (PLGA). The polymers in the disclosed composition do not however consist solely of PLA, PGA or PLGA, although any of these polymers can be used in combination with any of high molecular weight caprolactone polymer. When a second such polymer (aside from the polysaccharide polymer) is used, it is entangled with but not copolymerized with the high molecular weight polycaprolactone molecules. In a non-limiting example, a composition includes PLA as a second such polymer. In another non-limiting example, a composition includes PLGA as a second such polymer. In another non-limiting example, a composition includes PLGA as the second such polymer and PLCL as the high molecular weight polycaprolactone polymer. In such a composition, the PLGA can be a 75:25 (w/w) copolymer of polylactic acid and poly-glycolic acid, and the PLCL can be a 70:30 (w/w) copolymer of polylactic acid and polycaprolactone. In a composition comprising PLGA and PLCL, the two polymers can be combined at a w/w ratio of about 1:1, 1:2,1:3, 2:1, 2:3, 3:1, or 3:2; or about 1:3 to about 3:2; or about 3:2 to about 3:1.

In any of the disclosed compositions, the polysaccharide polymer molecules can be derived from a bacterial source or chemically synthesized, and/or can comprise sulfated or non-sulfated polysaccharide polymer molecules or any combination thereof. The polysaccharide polymer molecules can be oxidized, and/or covalently cross-linked, or otherwise modified or derivatized. Polysaccharide polymer molecules can comprise for example cellulose, inulin, starch, heparin, and/or one or more glycosaminoglycans (GAGs), such as but not limited to chitin, hyaluronic acid (HA), chondroitin, dermatan, chondroitin/dermatan, keratan, heparan, heparan, dextran, alginate, or any combination thereof. Any polysaccharide polymer molecules used in the composition can be sulfated or non-sulfated polysaccharide polymer molecules, or can be a combination thereof. Sulfated polysaccharides that can be used for the polysaccharide polymer molecules include, for example, chondroitin sulfate, dermatan sulfate, keratan sulfate, heparan sulfate, and dextran sulfate, or any combination thereof, or any combination of any of the foregoing sulfated polysaccharides with any non-sulfated polysaccharide. The polysaccharide molecules may include any of the foregoing existing as multiple polymers, for example in solution.

A composition according to the present disclosure can include the high molecular weight polycaprolactone polymer molecules and the polysaccharide polymer molecules in a w/w ratio of about 99:1 to 1:99 (weight of high molecular weight polycaprolactone polymer molecules to weight of polysaccharide polymer molecules), or from about 5:1 to about 10:1. In compositions including a second polymer such as polylactic acid, polyglycolic acid, or a copolymer of polylactic acid and polyglycolic acid, which is not copolymerized with the high molecular weight caprolactone polymer, the combined weight of the high molecular weight polycaprolactone polymer molecules and the weight of second polymer molecules equals a total polymer weight, and the weight ratio of the total polymer weight to the weight of the polysaccharide polymer molecules can be from about 99:1 to 1:99, or from about 5:1 to 10:1.

In non-limiting example, a hyaluronic acid polymer is used for the polysaccharide. Hyaluronic acid polymers may be obtained from a commercial source, such as a hyaluronic acid distributed by Lifecore Biomedical, Inc, Chaska, MN and having an average molecular weight of from about 100,000 to about 2,000,000 Daltons. In non-limiting example, the hyaluronic acid may be sodium hyaluronate having an average molecular weight of about 1,700,000. Compositions disclosed herein encompass those comprising the high molecular weight polycaprolactone polymer molecules and HA molecules in a w/w ratio of about 99:1 to 1:99 (weight of high molecular weight polycaprolactone polymer molecules to weight of HA molecules), or from about 5:1 to about 10:1. Similarly, compositions disclosed herein encompass those comprising the high molecular weight polycaprolactone polymer molecules and a second polymer which together have a combined weight which is the total polymer weight, combined with HA molecules in a w/w ratio of about 99:1 to 1:99 (total polymer weight to the weight of the HA molecules), or from about 5:1 to about 10:1. The disclosed compositions also encompass any composition as disclosed herein, wherein the HA polymer molecules comprise about 5% to about 20% by weight of the composition, or about 8% to about 12% by weight of the composition.

The compositions disclosed herein include one or more biologically active agent, such as but not limited to demineralized bone matrix (DBM), DBM cortical powder, crushed cancellous bone, platelets, platelet lysate, platelet rich plasma, bone marrow aspirate, chondrogenic cells and bioglass, a growth factor, a collagen such as type I collagen, type II collagen, type IX collagen, type X collagen, or type XI collagen, or any combination thereof. Any biologically active agent may be synthetic, for example obtained by prior synthesis or by recombinant protein production as known in the art, or by isolation from a natural source such as allogenic bone. A growth factor can be, in non-limiting example, a fibroblast growth factor (FGF) such as acidic FGF or basic fibroblast growth factor (bFGF), FGF2, or FGF-18; a member of the TGF-β superfamily such as transforming growth factor (TGF-β), TGF-β2, TGF-β3; a bone morphogenetic protein such as BMP-1, BMP-2, BMP-3, BMP-4, BMP-5, BMP-6 or BMP-7; a growth differentiation factor; ADMP-1; EGF, Pleotrophin, SDF-1; a hedgehog protein such as indian hedgehog, sonic hedgehog, or desert hedgehog; an insulin-like growth factor; an activin; a member of the insulin-like growth factor (IGF) family, such as IGF-I or IGF-II; a member of the platelet-derived growth factor (PDGF) family, such as PDGF-AP, PDGF-BB and PDGF-AA; a member of the interleukin (IL) family, such as IL-1, IL-2, IL-3, IL-4, IL-5 or IL-6; or a member of the colony-stimulating factor (CSF) family, such as CSF-1, G-CSF, and GM-CSF; or any combination thereof. For example, and without being limited by theory, certain growth factors are believed to promote formation of hyaline cartilage by promoting differentiation of mesenchymal stem cells into hyaline cartilage-forming chondrocytes, thereby speeding the healing process. BMP-2, BMP-4, and BMP-7, or any combination thereof, can for example be used in any composition. A flexible tissue matrix as described herein may comprise for example a type I collagen and/or a type II collagen alone or in combination with any other biologically active agent disclosed herein.

It should be understood that various combinations of biologically active agents are contemplated. For example, any osteostimulative agent, such as a bone morphogenetic protein can be used as the biologically active agent, alone or in combination with other biologically active agents or materials such as a collagen, allogenic bone, crushed cancellous bone, crushed cortical bone, or a DBM composition. Additionally, chondrogenic cells can include for example adult neuronal stem cells, chondrocytes, notochordal cells, mesenchymal stem cells, induced pluripotent stem cells, or any combination thereof. Mesenchymal stem cells can be derived as known in the art from various tissues including bone marrow, adipose tissue, synovium, periosteum, postpartum connective tissue, placenta, cord blood, and umbilical cord. Any tissues or derivatives of tissues that provide a source of the biologically active agent, such as a source of chondrogenic cells, or a source of a growth factor, can be allogenic. For example, a growth factor such as a bone morphogenetic protein can be isolated from a biological tissue source such as allogenic bone. Suitable cells such as chondrocytes can also be obtained from juvenile donor tissue or cadaver tissue, and can be from a cadaver of a juvenile individual. Thus, in any of the disclosed compositions, the biologically active agent can comprise cells alone or in combination with another biologically active agent as disclosed herein.

Any biologically active agent can be incorporated in the composition by first preparing an aqueous solution or suspension of the biologically active agent (e.g., a suspension), and adding the solution or suspension to the combination of the total polymer in organic solvent and the polysaccharide in water, before or during the emulsification process.

Any of the disclosed compositions can further comprise a flexibility agent. A flexibility agent can be present in the composition at any w/w ratio from about 9:1 to 99:1 (ratio of the weight of the high molecular weight caprolactone polymer molecules to the weight of the flexibility agent). A flexibility agent can be selected from, for example, triethyl citrate, acetyl tributyl citrate, acetyl triethyl citrate, tributyl citrate, trimethyl citrate, trihexyl citrate, acetyl trihexyl citrate, trioctyl citrate, acetyl trioctyl citrate, polyethylene glycol, polyethylene glycol monoalkyl ether, propylene glycol, glycerin, triacetin, and any combination thereof. A flexibility agent can used in compositions including the high molecular weight polycaprolactone polymer and a second polymer as disclosed herein. Given a total polymer weight which is the sum of the weight of the high molecular weight polycaprolactone polymer and the weight of any second polymer (which is not co-polymerized with the high molecular weight polycaprolactone polymer) which is included in the composition, the flexibility agent can be added to the composition at a weight ratio of the total polymer weight to the flexibility agent of about 9:1 to about 99:1. For example, in a composition comprising polylactic acid and a copolymer of polyglycolic acid and polycaprolactone, the weight of each in the composition combined would be the total polymer weight.

In non-limiting example, a composition comprises molecules of a high molecular caprolactone weight polymer such as, but not limited to a co-polymer of polylactic acid and polycaprolactone (poly(lactide-co-caprolactone), and molecules of hyaluronic acid polymers. The molecules of both types of polymers (high molecular caprolactone weight polymers and hyaluronic acid polymers) are entangled with another via the dual solvent emulsion process described herein. In such a composition, the HA polymer molecules have an HA weight, and the weight of the second polymer molecules (not copolymerized with the high molecular weight polycaprolactone polymer molecules) together with the weight of the high molecular weight polycaprolactone polymer molecules combined are a total polymer weight, and the ratio of the total polymer weight to the total HA weight in the composition is from about 99:1 to about 1:99, and in one example is about 5:1 to about 10:1.

In another non-limiting example, a composition comprises high molecular weight polycaprolactone molecules, hyaluronic acid molecules, and polylactic acid molecules as a second polymer that is entangled with but not copolymerized with the high molecular weight polycaprolactone molecules. In such a composition, the weight ratio of the polylactic acid to the copolymer of polyglycolic acid and polycaprolactone in the composition can be from about 9:1 to about 1:9, or from about 3:1 to about 7:3. As disclosed above, such a composition can further comprise a flexibility agent, wherein the polylactic acid and the copolymer of polyglycolic acid and polycaprolactone combined have a total polymer weight, and the weight ratio of the total polymer weight to the flexibility agent is about 9:1 to about 99:1.

In another non-limiting example, a composition comprises high molecular weight caprolactone polymer molecules comprising PLCL molecules, hyaluronic acid (HA) polymer molecules and PLGA molecules, wherein the PLGA molecules are not copolymerized with the high molecular weight polycaprolactone polymer molecules, and wherein the PLCL, HA and PLGA molecules are entangled together by a dual solvent emulsion process and combined with at least one biologically active agent to form a flexible matrix having a flexibility at a room temperature, wherein the room temperature flexibility is maintained when the flexible matrix is cooled to a temperature of less than about 20° C. In such a composition, the HA polymer molecules can have a total HA weight, and the polyester polymer molecules not copolymerized with the high molecular weight polycaprolactone polymer molecules, together with the high molecular weight polycaprolactone polymer molecules can have a total polyester weight, and the composition can be prepared such that the ratio of the total polyester weight to the total HA weight in the composition is from about 99:1 to about 1:99. The HA polymer molecules can comprise about 5% to about 20% by weight of the composition, and preferably about 8% to about 12% by weight of the composition.

Any composition disclosed herein can be used for the repair of defects in body tissues of a subject, including but not limited to cartilage and bone, and can be characterized by the ability to maintain a flexibility exhibited at room temperature after being cooled to a temperature of less than about 20° C., less than about 15° C., less than about 10° C., or less than about 5° C. down to about 0° C. Compositions disclosed herein can maintain flexibility within any selected narrower range from below about 20° C. down to about 0° C., for example at a temperature range of about 0° C. to about 15° C., about 5° C. to about 15° C., about 0° C. to about 10° C., about 5° C. to about 15° C., or about 10° C. to about 20° C.

Without wishing to be bound by theory, the high molecular weight caprolactone polymer molecules can be selected and combined with the polysaccharide polymers in a ratio that results in a gel temperature of the combined polymers of below about 20° C., or below about 15° C., 10° C., or 5° C. down to about 0° C., or within any of the foregoing temperature ranges, so that the composition maintains the flexibility exhibited at room temperature when cooled to a temperature below any of the foregoing temperatures, or within any of the foregoing temperature ranges. It should be understood then, that a composition that maintains its room temperature flexibility when cooled below a certain temperature includes high molecular weight caprolactone polymer molecules (of one molecular species or a combination of molecular species) which, when entangled with the polysaccharide polymer molecules as described herein, result in a composition having a gel temperature or gel temperature range, which corresponds to that temperature at which, or temperature range within which, the composition loses or starts to lose the flexibility it exhibits at room temperature.

Any of the compositions described herein can therefore be characterized by a flexibility exhibited when the composition is at about room temperature, i.e., at least above about 20° C. It will be understood that "room temperature" as used herein can vary, but will not be less than about 20° C., and for example is no more than about 26° C. (i.e., is between about 68° F. and about 79° F.), and has an average of about 23° C. (73° F.).

It should further be understood that flexibility of the compositions disclosed herein can be measured using methods known in the mechanical sciences, and/or by the observation and manual testing by one of average skill in the art. It will be clear for example to the skilled worker from manual handling of a composition whether the flexibility of the composition is greater, less or about the same as the temperature of the composition changes. The same holds true for the compressive resistance and conformability of any composition.

For example, a composition that maintains its room temperature flexibility when cooled below room temperature, i.e., below about 20° C., or for example to a temperature of about 0° C. to about 15° C., can include high molecular weight polycaprolactone polymer molecules of a single species or a combination of species entangled with polysaccharide molecules by a dual solvent emulsion process as described herein, such that the gel temperature of the composition is below about 20° C., below about 15° C., below about 10° C., or below about 5° C. down to about 0° C., or in the range of about 0° C. to about 15° C., about 5° C. to about 15° C., about 0° C. to about 10° C., about 5° C. to about 15° C., or about 10° C. to about 20° C.

A composition of the present disclosure is prepared using a dual solvent emulsion process as described herein below and in the Examples. Briefly, a high molecular weight caprolactone polymer is dissolved in an organic solvent such as ethyl acetate, a halogenated solvent such as methylene dichloride, chloroform, or tetrahydrofuran, or any combination thereof as known to those of routine skill in the art. Once the high molecular weight caprolactone polymer is dissolved, optionally a polyester polymer such as PLA, PGA or PLGA may be added to the solution and also dissolved. When a high molecular weight polycaprolactone polymer is combined with another (second) polymer such as PGA, PLA or PLGA, they may be combined in a volume ratio of about 10:1 to about 1:1 (second polymer:high molecular weight polycaprolactone polymer). For example, PLGA may be combined with PLCL at a volume ratio of about 10:1 to about 1:1 (PLGA:PLCL).

The polysaccharide such as but not limited to hyaluronic acid (HA) is dissolved in water. For example, the high molecular weight caprolactone polymer molecules and the polysaccharide molecules are present in the composition at a weight:weight ratio of from about 99:1 to about 1:99 (high molecular weight caprolactone polymer molecules to polysaccharide molecules).

The two solutions (total polymer including high molecular weight polycaprolactone and any second polymer in organic solvent, and polysaccharide in water) are combined at a volume ratio of at least about 1.5:1 (3:2), about 2:1, about 3:1, or any volume ratio from about 4:1 to about 15:1 (total polymer including high molecular weight polycaprolactone in organic solvent:polysaccharide in water) and mixed using any agitation method as known in the art to form an emulsified mixture, or emulsion. For example, a homogenizer as known in the art can be used for agitation. The emulsion is then frozen. After freezing, the frozen emulsion is lyophilized to remove the two solvents, thereby yielding a matrix comprising the high molecular weight caprolactone polymer, and optionally a polyester polymer such as PLA, PGA or PLGA, entangled with the polysaccharide. As described in further detail herein below, prior to freezing, a certain volume of the emulsion can optionally be poured into a flat mold of predetermined volume such that the certain volume of emulsion results in a layer of emulsion of a desired thickness. After freezing and lyophilizing, the resulting matrix is formed as a thin film or membrane of the desired thickness, which is then removed from the mold for use in repairing tissue, or for further processing to achieve a desired membrane thickness, for example using rollers.

As disclosed herein, any composition according to the present disclosure optionally further includes one or more flexibility agents to promote or further enhance the flexibility of the tissue matrix. The flexibility agent may be added to either the total polymer including high molecular weight polycaprolactone in organic solvent, or to the aqueous polysaccharide solution, depending on the solubility characteristics of the flexibility agent as will be readily known or determined by one of routine skill in the art.

Any composition disclosed herein can be formed as a membrane for convenient implantation at the site of a tissue defect. For example, a composition may be prepared and formed as a membrane having a thickness of at least about 0.5 mm up to about 3 mm. A membrane may be formed using methods known to those of routine skill in the art for preparing thin films from liquid or fluid materials. For example, a membrane may be formed by preparing the dual solvent emulsion as described elsewhere herein, pouring a certain volume of the emulsion into a mould of predetermined size, and then lyophilizing the emulsion in the mould. Thickness of the membrane can be further controlled by regulating the rate of pour into the mould and stopping the pour when a layer of emulsion of desired thickness within the mould is obtained. After the lyophilized emulsion has been removed from the mould, the thickness of the resulting membrane can still further be modified by rolling the material through rollers to obtain a membrane of the desired thickness. Alternatively, a membrane may be formed using an extrusion process in which the emulsion is extruded at a predetermined thickness.

C. Methods

Any of the compositions disclosed herein can be characterized by the ability to promote growth of cells in vivo or ex vivo when contacted with cells in vivo or ex vivo. The compositions disclosed herein can be characterized as a porous matrix having pores with a shape and structure exhibited when the matrix is dry, and further characterized by (i) retention of the pore structure and shape when hydrated and (ii) the ability to support the growth of cells in vivo or ex vivo when contacted with cells in vivo or ex vivo. Thus, the compositions disclosed herein can be used to repair tissue by implanting implants formed from the matrix into a tissue defect, and also can be used to support cell and tissue growth ex vivo, for example in vitro to support growth of engineered tissue for later use in tissue repair.

The present disclosure encompasses a method for repairing a tissue defect in a subject in need thereof, comprising applying to the tissue defect any composition as disclosed herein, or any implant or membrane formed from any composition as disclosed herein. For example, the method can comprise implanting into the tissue defect a strip or membrane formed from any composition as disclosed herein. The method may comprise surgical exposure of the tissue defect to provide access for the implantation.

The subject can be any animal suffering from a tissue defect that can be benefit from such treatment, including a human or a non-human animal, including non-human mammal such as but not limited to a non-human primate including monkeys and apes, a canine including domesticated dogs, a feline including domesticated house cats, and livestock animals including any bovine, equine, porcine, bovidae including sheep and goats, and camelidae. Specifically contemplated are methods for treating human subjects.

The compositions disclosed herein can be used to treat a variety of tissue defects, including but not limited to tissue defects comprising one or both of a bone defect and a cartilage defect. The methods can be used for example to repair a tissue defect in a joint of the subject. Defects which may be treated may be any form of joint defect involving loss of or damage to hyaline cartilage, such as, but not limited to, a full-thickness defect, a partial-thickness defect, an age-related degenerative disease defect such as osteoarthritis, a congenital defect, or an injury resulting from trauma.

For example, the tissue defect may comprise one or both of a bone defect and a cartilage defect in a joint of the subject. In a human subject, any such joint can be treated using the disclosed methods, including but not limited to an ankle, knee, hip, sacroiliac joint, elbow, wrist, shoulder, jaw (temporomandibular), knuckle, interphalangeal joint, and atlanto-occipital joint, atlanto-axial joint, and intervertebral joint. The present disclosure also contemplates using the compositions and methods disclosed herein to repair any joint in a non-human animal, which may or may not have a counterpart among the foregoing list of human joints.

Once implanted in vivo, the flexible tissue matrix serves as scaffold that provides a microenvironment that is both biocompatible with and conducive to new bone formation. The high molecular weight polymer and optional additional (second) polymer provide(s) a three-dimensional structure, and a reliable resorption rate at the site of implantation which is consistent with the rate of endochondral bone remodeling. Additionally, a polysaccharide such as hyaluronic acid is believed to play an important role in tissue regeneration and repair, and to assist important early events in bone formation by promoting the migration, proliferation, and differentiation of osteogenic cells. A combination of a high molecular weight caprolactone polymer with a polysaccharide such as hyaluronic acid, and optionally further with a second polymer such as PLA, PGA or PLGA, when entangled according to the process described herein, provides a scaffold with improved cohesiveness, molding properties and handling characteristics relative to other known synthetic scaffolds and matrices.

The present teachings encompass methods for repairing a full-thickness chondral defect in a joint of a patient in need of treatment. Such a method may be applied to the repair any body joint comprising hyaline cartilage, such as, but not limited to, a joint of a knee, an elbow, an ankle, a shoulder, a jaw or a wrist. A joint may be any joint comprising articular cartilage, such as a joint of a long bone, for example a knee joint comprising articular cartilage of a femur.

Treatment of a joint defect using the methods disclosed herein is believed to promote deposition of hyaline cartilage in the defect rather than fibrocartilage. Briefly, the methods comprise contacting the joint with, or introducing into the joint, cells which may differentiate into chondrocytes, such as mesenchymal stem cells, and applying to the joint a membrane comprising a flexible tissue matrix as described herein. Such methods using a tissue matrix comprising only a polyester polymer and hyaluronate are described for example in U.S. 2007-0128155 A1 (U.S. patent application Ser. No. 11/635,265) the entire disclosure of which is herein incorporated by reference. Most conveniently, such mesenchymal stem cells may be autologous mesenchymal stem cells originating in the bone underlying the damaged joint, although mesenchymal stem cells from other bones may be used as well. Contact between the damaged joint and autologous mesenchymal stem cells from the underlying bone may be achieved most readily by a microfracture technique, i.e. by introducing one or more apertures into the subchondral bone underlying the defective joint. Such apertures need be at least large enough to allow passage of the mesenchymal stem cells from the bone mesenchyme to the joint. Several well-established procedures may be used to form such passages, such as, without limitation, abrasion (such as abrasion arthroplasty), perforation (e.g., with a surgical awl) and drilling of the bone. These and other treatment procedures are well known to skilled artisans, and described in detail in the literature, for example in references such as Steadman, J. R. et al., Clinical Orthopaedics and Related Research 391S: S362-S369, 2001; and Steadman et al., J. Knee Surg. 15(3):170-176 (2002).

Without being limited by theory, it is believed that following introduction of passages or perforations into the bone, mesenchymal stem cells may migrate out from the bone marrow cavity through the passages, and populate the joint. Exposure of the mesenchymal stem cells to the local environment of the joint leads to differentiation of the stem cells into cartilage-forming chondrocytes. In the further presence of a membrane comprising a tissue matrix as described herein, the chondrocytes produce hyaline cartilage rather than fibrocartilage. The introduction of the cells under these conditions may thereby restore the cartilage of a defective joint to a state more closely resembling that of the joint pre-injury.

Accordingly, the methods of the present disclosure may include microfracturing bone underlying the joint, and applying to the joint a membrane comprising a flexible tissue matrix as described herein. Microfracturing may precede the application to the joint of a membrane comprising a flexible tissue matrix, or vice versa. Additionally, the membrane can be manually shaped according to the contours of a joint. The method may further comprise securing the membrane to the joint, for example anchoring or fastening the membrane to the joint, or immobilizing the membrane at the joint.

Securing the membrane may be part of the surgical intervention in the treatment of a patient. Accordingly, in various aspects, a skilled artisan such as an orthopaedic surgeon may secure a membrane at the site of defect in a patient, using at least one fastener, to thereby retain the membrane at the site. Such retention of the membrane may promote the formation of hyaline cartilage by chondrocytes differentiated from mesenchymal stem cells. Examples of a fastener that may be used in the present methods include, without limitation, a biocompatible glue, a suture, a tissue weld, a dart, a staple, a screw, a tack, and a combination thereof. A biocompatible glue may be a fibrin glue, such as a fibrin sealant. A non-limiting example of a biocompatible glue that may be used with the present teachings is a fibrin sealant manufactured by Oesterreichisches Institut Fuer Haemoderivate G.M.B.H. in Vienna, Austria and distributed by Baxter Healthcare Corporation, Glendale, CA under the brand name TISSEEL® VH. Non-limiting examples of other fasteners which may be used instead of, or in addition to a biocompatible glue include sutures, tissue welds such as described in Helmsworth, T. F., et al., Laser Surgery Medicine 10: 576-583, 1990, staples, darts, pins and tacks. In some aspects, a fastener may comprise a biocompatible or bioabsorbable material such as, without limitation, a PLA/PLG polymer, or a non-absorbable material such as a biocompatible metal. A fastener may be an absorbable suture which passes through both the membrane and a joint, and thereby secures apposition of the membrane to the joint. Furthermore, in non-limiting example, the attaching may comprise gluing the membrane to the joint.

As indicated in the foregoing, introduction of at least one aperture in the subchondral bone may precede application of a membrane to the joint, or application of a membrane to the joint may precede the introduction of at least one aperture.

The present disclosure thus encompasses methods for repair of a full thickness chondral defect in a joint of a patient in need of treatment, the methods involving a) introducing at least one aperture through bone underlying the joint, wherein the at least one aperture allows migration of mesenchymal stem cells from a marrow cavity of the bone to the joint, and b) applying to the joint a membrane comprising a flexible tissue matrix as described herein. The methods may further comprise securing the membrane to the joint, using attachments methods and devices as described herein and as otherwise well known to skilled artisans.

Additionally, in use the flexible tissue matrix may be combined with one or more growth factors, osteostimulative agents, and/or bone morphogenetic proteins, and/or with other materials such as allogenic bone, crushed cancellous bone, crushed cortical bone, or a DBM composition. For example, any of the joint treatment or repair methods optionally further comprises applying to the joint, or implanting at a joint defect site, one or more growth factors, osteostimulative agents, and/or bone morphogenetic proteins, and/or other material such as allogenic bone, crushed cancellous bone, crushed cortical bone, or a composition composed of DBM. For example, a DBM gel, putty or paste, or thin sheets or membranes of DBM may be implanted at the joint defect site and/or placed in direct contact with the joint at the defect site. Several suitable DBM substances are commercially available for use in orthopedic surgeries, such as but not limited to Osteofil® IC allograft paste (RTI Biologics Inc., Alachua, Fla.), Grafton® DBM products including putty, paste, gel and sheets (strips) (Medtronics Biologics, Inc., Memphis Tenn.), Dynagraft D™ (Citagenix, Inc., Laval, Qc, Canada), and demineralized trabecular bone products such as but not limited to MatrixOI™ (Cellright, Inc., Universal City, Tex.) Sheets or strips comprising or made of any of the foregoing materials may for example have approximately the same thickness as a membrane comprising the flexible tissue matrix, e.g. at least about 0.5 mm up to about 3 mm. Any of the foregoing materials in any of their various forms may be used generally according to the manufacturer's instructions and in combination with the flexible tissue matrix as may be determined according to guidelines well known to those of routine skill in the art. Application to the joint, or implantation at the a joint defect site, of one or more growth factors, osteostimulative agents, and/or bone morphogenetic proteins, and/or with other materials such as allogenic bone, crushed cancellous bone, crushed cortical bone, or a DBM composition , or a composition comprising any one or more such elements, may take place at any point relative to application of the flexible membrane to the joint, and introduction of at least one aperture for microfracturing.

The following examples are illustrative, and are not intended to limit the scope of the claims.

EXAMPLES

Example 1

Entanglement of a Polyester, poly(lactide-co-glycolide) (PLGA) and a Polysaccharide (Hyaluronic Acid)

This example illustrates a method of constructing an entangled matrix comprising a polyester and a polysaccharide. In this example, poly(lactide-co-glycolide) having molecular weight of $1.5 \times 10^5$ is dissolved in dichloromethane (125 mg/ml) and with Hyaluronate (HyA) of molecular weight of about $1.3 \times 10^6$ Dalton is dissolved in water (15 mg/ml). The two polymer solutions, 2 parts PLGA, and 1 part HyA, are mixed with 1 part Milli Q water by vortexing at high speed for about 5 minutes. The emulsified mixture is immediately poured into a mould pre-cooled at $-70°$ C. in a bath containing dry ice in isopropyl alcohol. After freezing, the mold and its contents are transferred into a second container that is loaded with dry ice and connected to vacuum line. Organic solvent is removed by this process at the temperature between $-70°$ C. to $-40°$ C., leaving HyA in wet-ice phase. Water is then removed by raising the temperature to $-10°$ C. under vacuum.

Example 2

Entanglement of the High Molecular Weight Caprolactone Polymer poly(lactide-co-caprolactone (PLCL), and PLGA, and a Polysaccharide (Hyaluronic Acid)

In this example, poly(lactide-co-caprolactone) (PLCL) having a molecular weight of about $2 \times 10^5$ is dissolved in ethyl acetate (80 mg/ml) containing polyethylene glycol 400 (PEG400) (20 mg/ml). Once the PLCL is dissolved, poly (lactide-co-glycolide) (PLGA) having a molecular weight of about $1.5 \times 10^5$ is added (240 mg/ml) and dissolved. Hyaluronate (HyA) of molecular weight of about $1.5 \times 10^6$ is dissolved in water (20m g/ml). The two polymer solutions, 3 parts PLGA/PLCL, and 2 parts HyA, are mixed, poured in moulds sized sufficiently to produce a membrane having a thickness of 3 mm, and frozen as described in Example 1. After freezing, the frozen emulsion is lyophilized to remove the two solvents yielding a membrane formed of a flexible tissue matrix comprising PLGA/PLCL entangled with HyA.

Example 3

Treatment of a Knee Injury.

In this example, an athletic patient presents with a traumatic knee injury to an orthopedic surgeon. A diagnosis is made of damaged articular cartilage of the femoral condyle. The surgeon performs a microfracture procedure on the patient's femoral condyle, creating channels through the bone underlying the hyaline cartilage using an awl or drill. The surgeon selects a membrane having a thickness of 3 mm formed from a tissue matrix prepared as described in Example 2, and shaped to follow the contours of the condyle. The surgeon coats one side of the membrane with TISSEEL® VH fibrin sealant and then applies the membrane to the damaged femoral condyle using gentle pressure. The patient is instructed to keep pressure off the knee for a period of weeks. The condyle is repaired with new hyaline cartilage by six months after the surgical intervention.

Example 4

Treatment of a Knee Injury Using Composition in Combination with a DBM Composition Treatment of a knee injury is carried out substantially as described in Example 3 above. A membrane formed of DBM and having a thickness of no more than 3 mm is also applied to the damaged femoral condyle and secured in position using TISSEEL® VH fibrin sealant.

Example 5

Treatment of Osteoarthritis.

In this example, a patient with osteoarthritis presents with a full-thickness chondral defect in an elbow joint. A surgeon performs a microfracture procedure on the humerus underlying the joint using a drill or awl. A membrane having a thickness of 1 mm and formed from a tissue matrix prepared substantially as described in Example 2, and shaped to follow the contours of the condyle, is positioned by the surgeon upon the condyle. The surgeon secures the membrane in place with a series of screws made of a resorbable PLA/PLG polymer. Following surgery, new hyaline cartilage deposits along the condyle over a six month period. The new cartilage is anatomically indistinguishable from normal hyaline cartilage.

Example 6

Treatment of the Shoulder

In this example, a middle age male presents with a traumatic dislocation of the shoulder. A diagnosis is made of disruption of the articular cartilage covering the head of the humerus at its articulation with the glenoid socket of the scapula. The patient is operated upon by a surgeon, who performs a microfracture procedure on the head of the humerus. A membrane having a thickness of 1 mm and formed from a tissue matrix prepared as described in Example 2, and shaped to approximate the contours of the humeral head, is positioned by the surgeon upon the humeral head. The surgeon secures the membrane in place with a series of resorbable pins. Following surgery, new hyaline cartilage deposits along the condyle over a period of six months. The new cartilage is anatomically indistinguishable from normal hyaline cartilage.

One skilled in the art would readily appreciate that the articles and kits described in the present disclosure are well adapted to carry out the objects and obtain the ends and advantages mentioned, as well as those inherent therein. The methods, procedures, treatments and kits described herein are merely representative and exemplary, and are not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference. Any discussion of references cited herein is intended merely to summarize the assertions made by their authors and no admission is made that any reference or portion thereof constitutes relevant prior art. Applicants reserve the right to challenge the accuracy and pertinency of the cited references.

REFERENCES

Rodrigo J. I., et al., Osteoarticular injuries of the knee. pp. 2077-2082, In: Chapman, M. W. (ed): OPERATIVE ORTHOPAEDICS, Vol. 3, 2nd Ed. Lippincott, Philadelphia, Pa., 1993

Tippet J. W., Articular cartilage drilling and osteotomy in osteoarthritis of the knee, pp. 325-339, in: McGinty, J. B. (ed): Operative Arthroscopy. Raven Press, New York, N.Y., 1991

Vangsness, C. T., et al., Amer. I Orthop. 33 (2 Suppl): 29-34, 2004; Textbook of Arthroscopy, Miller, M. D. et al., ed. Saunders, 2004

The Adult Knee, Callaghan, J.1. et al., ed., Lippincott Williams & Wilkins, 2003;

Operative Treatment of Elbow Injuries, Baker, C. L., et al., ed., Springer, 2002

Osteoarthritis: Fundamentals and Strategies for Joint-preserving Treatment, Grifka, J. J., et al., ed., Springer, 2000

Reconstructive Surgery of the Joints, Morrey, B. F., et al., ed., Churchill Livingstone, 1996

Operative Arthroscopy, McGinty, J. B., et al., ed., Lippincott-Raven, 1996

The Knee, Scott, W. N., ed., Mosby-Year Book, 1994

Surgical Repair and Reconstruction in Rheumatoid Disease, Benjamin, A., et al., Spring-Verlag, 1993

The Knee: Form, Function, Pathology, and Treatment; Larson, R. L., et al., ed., W. B. Saunders, 1993

O'Connor's Textbook of Arthroscopic Surgery, Shahriaree, H., ed., I B. Lippincott, 1992.

What is claimed is:

1. A composition for supporting repair of biological tissues comprising: total polymers comprising caprolactone polymer molecules and at least one additional polyester polymer other than a caprolactone polymer which is not copolymerized with caprolactone polymer, wherein the total polymers are entangled with polysaccharide polymer molecules by a dual solvent emulsion process to form a dry flexible matrix, and at least one biologically active agent, said composition being formed by the steps consisting of:

a. dissolving the total polymers in an organic solvent;
   b. dissolving the polysaccharide in an aqueous solvent;
   c. combining the total polymers in the organic solvent with the polysaccharide in the aqueous solvent;

d. blending the total polymers in the organic solvent with the polysaccharide in the aqueous solvent to form the dual solvent emulsion;

e. removing the organic solvent and aqueous solvent from the emulsion to form a flexible matrix comprising the total polymer molecules entangled with polysaccharide polymer molecules; and f. adding the at least one biologically active agent to the composition at any of steps (c) or (d), wherein the weight ratio of the polyester polymer to the caprolactone polymer ranges from about 1:1 to about 4:1 and wherein the composition maintains the flexibility when cooled to at least about room temperature.

2. The composition of claim 1, wherein the at least one biologically active agent comprises an agent selected from the group consisting of: demineralized bone matrix (DBM), DBM cortical powder, crushed cancellous bone, platelets, platelet lysate, platelet rich plasma, bone marrow aspirate, chondrogenic cells, bioglass, a growth factor, and any combination thereof.

3. The composition of claim 1, wherein the at least one biologically active agent comprises chondrogenic cells.

4. The composition of claim 1, wherein the biologically active agent comprises cells selected from the group consisting of: adult neuronal stem cells, chondrocytes, notochordal cells, mesenchymal stem cells, and induced pluripotent stem cells.

5. The composition of claim 1, wherein the biologically active agent comprises mesenchymal stem cells derived from a source selected from the group consisting of: bone marrow, adipose tissue, synovium, periosteum, post-partum connective tissue, placenta, cord blood, and umbilical cord.

6. The composition of claim 1, wherein the polysaccharide polymer molecules comprise polysaccharide polymer molecules derived from a bacterial source or chemically synthesized.

7. The composition of claim 1, wherein the polysaccharide polymer molecules comprise hyaluronic acid (HA) polymer molecules.

8. The composition of claim 7, wherein the HA polymer molecules comprise about 5% to about 20% by weight of the composition.

9. The composition of claim 7, wherein the HA polymer molecules comprise about 8% to about 12% by weight of the composition.

10. The composition of claim 7, wherein the caprolactone polymer molecules and the hyaluronic acid polymers are present in the composition at a weight ratio of from about 99:1 to about 1:99 (caprolactone polymer molecules to HA polymer molecules).

11. The composition of claim 1, wherein the polysaccharide polymer molecules are oxidized.

12. The composition of claim 1, wherein the polysaccharide polymer molecules are covalently cross-linked.

13. The composition of claim 1, wherein the at least one biologically active agent comprises at least one growth factor.

14. The composition of claim 13, wherein the at least one growth factor comprises a bone morphogenetic protein.

15. The composition of claim 13, wherein the at least one growth factor is an isolated growth factor previously isolated from allogenic bone.

16. The composition of claim 13, wherein the at least one growth factor is selected from the group consisting of basic fibroblast growth factor (bFGF), FGF2, FGF-18, transforming growth factor (TGF-$\beta$), BMP-2, BMP-4, BMP-7, ADMP-1, PDGF-bb, EGF, Pleotrophin, SDF-1, a hedgehog protein, an insulin-like growth factor, a platelet-derived growth factor, an interleukin, a colony-stimulating factor, and an activin.

17. The composition of claim 1, wherein the at least one biologically active agent comprises a type I collagen or a type II collagen.

18. The composition of claim 1, wherein the composition has a flexibility at about room temperature and maintains the flexibility when cooled to a temperature of less than about 20° C.

19. The composition of claim 18, wherein the composition maintains the flexibility when cooled to a temperature of about 0° C. to about 15° C.

20. The composition of claim 18, further comprising polyester polymer molecules not copolymerized with the caprolactone polymer molecules, the polyester molecules entangled with the caprolactone polymer molecules and the polysaccharide polymer molecules by the dual solvent emulsion process.

21. The composition of claim 20, wherein the polyester polymer molecules comprise at least one polymer selected from the group consisting of: polylactic acid, polyglycolic acid, and a copolymer of polylactic acid and polyglycolic acid (PLGA).

22. The composition of claim 21, wherein the caprolactone polymers comprise a copolymer of polyglycolic acid and caprolactone, and the polyester polymers comprise polylactic acid.

23. The composition of claim 22, wherein the weight ratio of the polylactic acid to the copolymer of polyglycolic acid and caprolactone in the composition is from about 3:1 to about 7:3.

24. The composition of claim 22, further comprising a flexibility agent, wherein the polylactic acid and the copolymer of polyglycolic acid and caprolactone combined have a total polymer weight, and the weight ratio of the total polymer weight to the flexibility agent is about 9:1 to about 99:1.

25. The composition of claim 24, wherein the flexibility agent is selected from the group consisting of triethyl citrate, acetyl tributyl citrate, acetyl triethyl citrate, tributyl citrate, trimethyl citrate, trihexyl citrate, acetyl trihexyl citrate, trioctyl citrate, acetyl trioctyl citrate and any combination thereof.

26. The composition of claim 24, wherein the flexibility agent is selected from the group consisting of polyethylene glycol, polyethylene glycol monoalkyl ether, propylene glycol, glycerin, triacetin and any combination thereof.

27. The composition of claim 18, wherein the polysaccharide polymer molecules comprise HA polymer molecules.

28. The composition of claim 27, wherein the HA polymer molecules comprise about 5% to about 20% by weight of the composition.

29. The composition of claim 27, wherein the HA polymer molecules comprise about 8% to about 12% by weight of the composition.

30. The composition of claim 27, wherein the HA polymer molecules have a total HA weight, and wherein the polyester polymer molecules not copolymerized with the caprolactone polymer molecules, together with the caprolactone polymer molecules have a total polymer weight, wherein the ratio of the total polymer weight to the total HA weight in the composition is from about 1:1 to about 4:1.

31. The composition of claim 30, wherein the ratio of the total polyester weight to the total HA weight in the composition is from about 5:1 to about 10:1.

32. The composition of claim 20, wherein the polyester polymer molecules comprise PLGA.

33. The composition of claim 32, wherein the caprolactone polymers comprise poly (L-lactide-co-caprolactone) (PLCL).

34. The composition of claim 33, wherein the PLGA is PLGA (75:25), and the PLCL is (70:30).

35. The composition of claim 33 or 34, wherein the PLGA and PLCL are combined at a w/w ratio of about 2:1 to about 3:2.

36. The composition of claim 33 or 34, wherein the PLGA and PLCL are combined at a w/w ratio of about 3:2 to about 3:1.

37. The composition of claim 1, wherein the caprolactone polymer molecules entangled with the polysaccharide polymers form a polymer matrix having a gel temperature below about 20° C.

38. The composition of claim 1, wherein the caprolactone polymer molecules are selected from polycaprolactone; a co-polymer of polylactic acid and polycaprolactone; a co-polymer of polyglycolic acid and polycaprolactone; a copolymer of polylactic acid, polyglycolic acid, and polycaprolactone; a co-polymer of polyethylene glycol, polylactic acid and polycaprolactone; a co-polymer of polyethylene glycol, polyglycolic acid and polycaprolactone; and a copolymer of polyethylene glycol, polylactic acid, polyglycolic acid, and polycaprolactone.

39. The composition of claim 38, comprising a co-polymer selected from a copolymer of polylactic acid and polycaprolactone; a co-polymer of polyglycolic acid and polycaprolactone; a copolymer of polylactic acid, polyglycolic acid and polycaprolactone; a co-polymer of polyethylene glycol, polylactic acid and polycaprolactone; a co-polymer of polyethylene glycol, polyglycolic acid and polycaprolactone; and a copolymer of polyethylene glycol, polylactic acid, polyglycolic acid, and polycaprolactone.

40. The composition of claim 1, further comprising at least one flexibility agent.

41. The composition of claim 40, wherein the w/w ratio of the caprolactone polymer molecules to the flexibility agent in the composition is about 9:1 to 99:1.

42. The composition of claim 40, wherein the flexibility agent is selected from the group consisting of triethyl citrate, acetyl tributyl citrate, acetyl triethyl citrate, tributyl citrate, trimethyl citrate, trihexyl citrate, acetyl trihexyl citrate, trioctyl citrate, acetyl trioctyl citrate and any combination thereof.

43. The composition of claim 40, wherein the flexibility agent is selected from the group consisting of polyethylene glycol, polyethylene glycol monoalkyl ether, propylene glycol, glycerin, triacetin and any combination thereof.

44. The composition of claim 1, further characterized by the ability to promote growth of cells in vivo or ex vivo when contacted with cells in vivo or ex vivo.

45. A membrane comprising the composition of claim 1, wherein the membrane has a flexibility at about room temperature and maintains the flexibility when cooled to a temperature of less than about 20° C.

46. The membrane of claim 45, wherein the membrane maintains the flexibility when cooled to a temperature of about 0° C. to about 15° C.

47. The membrane of claim 45, wherein the membrane further has a compressive resistance and a conformability at room temperature, and wherein the membrane maintains the room temperature compressive resistance and conformability when cooled to a temperature of less than about 20° C.

48. The membrane of claim 47, wherein the membrane further has a compressive resistance and a conformability at room temperature, and wherein the membrane maintains the room temperature compressive resistance and conformability when cooled to a temperature of about 0° C. to about 15° C.

49. The membrane of claim 45, having a thickness of at least about 0.5 mm up to about 3 mm.

50. A composition for supporting repair of a tissue defect in a subject, comprising: hyaluronic acid (HA) polymer molecules and a polymer mixture comprising poly (L-lactide-co-caprolactone) (PLCL) molecules and PLGA molecules, wherein the PLGA molecules are not copolymerized with the PLCL molecules, and wherein the PLCL, HA and PLGA molecules are entangled together by a dual solvent emulsion process and combined with at least one biologically active agent to form a dry flexible matrix, said composition being formed by the steps consisting of:
 a. dissolving the polymer mixture in an organic solvent;
 b. dissolving the HA molecules in an aqueous solvent;
 c. combining the polymer mixture in the organic solvent with the HA molecules in the aqueous solvent;
 d. blending the polymer mixture in the organic solvent with the HA molecules in the aqueous solvent to form the dual solvent emulsion;
 e. removing the organic solvent and aqueous solvent from the emulsion to form a flexible matrix comprising the polymer mixture molecules entangled with the HA molecules; and
 f. adding the at least one biologically active agent to the composition at any of steps (c) or (d);
wherein the flexible matrix has a flexibility at a room temperature, wherein the room temperature flexibility is maintained when the flexible matrix is cooled to a temperature of less than about 20° C., and wherein the HA polymer molecules have a total HA weight, and wherein the PLGA molecules not copolymerized with the PLCL molecules, together with the PLCL molecules have a total polymer weight, wherein the ratio of the total polymer weight to the total HA weight in the composition is from about 1:1 to about 4:1.

51. The composition of claim 50, wherein the HA polymer molecules comprise about 5% to about 20% by weight of the composition.

52. A composition for supporting repair of biological tissues comprising: total polymers comprising caprolactone polymer molecules and at least one additional polyester polymer other than a caprolactone polymer which is not copolymerized with caprolactone polymer, wherein the total polymers are entangled with polysaccharide polymer molecules by a dual solvent emulsion process to form a dry flexible matrix, and at least one biologically active agent, said composition being formed by the steps consisting essentially of:
 a. dissolving the total polymers in an organic solvent;
 b. dissolving the polysaccharide in an aqueous solvent;
 c. combining the total polymers in the organic solvent with the polysaccharide in the aqueous solvent;
 d. blending the total polymers in the organic solvent with the polysaccharide in the aqueous solvent to form the dual solvent emulsion;
 e. removing the organic solvent and aqueous solvent from the emulsion to form a flexible matrix comprising the total polymer molecules entangled with polysaccharide polymer molecules; and
 f. adding the at least one biologically active agent to the composition at any of steps (c) or (d), wherein the weight ratio of the polyester polymer to the caprolactone polymer
ranges from about 1:1 to about 4:1 and wherein the composition maintains the flexibility when cooled to at least about room temperature.

53. A composition for supporting repair of a tissue defect in a subject, comprising: hyaluronic acid (HA) polymer molecules and a polymer mixture comprising poly (L-lactide-co-caprolactone) (PLCL) molecules and PLGA molecules, wherein the PLGA molecules are not copolymerized with the PLCL molecules, and wherein the PLCL, HA and PLGA molecules are entangled together by a dual solvent emulsion process and combined with at least one biologically active agent to form a dry flexible matrix, said composition being formed by the steps consisting essentially of:
   a. dissolving the polymer mixture in an organic solvent;
   b. dissolving the HA molecules in an aqueous solvent;
   c. combining the polymer mixture in the organic solvent with the HA molecules in the aqueous solvent;
   d. blending the polymer mixture in the organic solvent with the HA molecules in the aqueous solvent to form the dual solvent emulsion;
   e. removing the organic solvent and aqueous solvent from the emulsion to form a flexible matrix comprising the polymer mixture molecules entangled with the HA molecules; and
   f. adding the at least one biologically active agent to the composition at any of steps (c) or (d);
wherein the flexible matrix has a flexibility at a room temperature, wherein the room temperature flexibility is maintained when the flexible matrix is cooled to a temperature of less than about 20° C., and wherein the HA polymer molecules have a total HA weight, and wherein the PLGA molecules not copolymerized with the PLCL molecules, together with the PLCL molecules have a total polymer weight, wherein the ratio of the total polymer weight to the total HA weight in the composition is from about 1:1 to about 4:1.

54. A method for repairing a tissue defect in a subject in need thereof, the method comprising: applying to the tissue defect the composition of any one claim 1, or the membrane of claim 45.

55. The method of claim 54, wherein the subject is a non-human mammal.

56. The method of claim 54, wherein the subject is a human.

57. The method of claim 54, wherein the tissue defect is a bone defect or a cartilage defect.

58. The method of claim 54, wherein the tissue defect comprises at least one of a bone defect and a cartilage defect.

59. The method of claim 58, wherein the tissue defect comprises a bone defect and a cartilage defect.

60. The method of claim 58, wherein the tissue defect is in a joint of the subject.

61. The method according to claim 60, wherein the joint is selected from the group consisting of: ankle, knee, hip, sacroiliac joint, elbow, wrist, shoulder, jaw (temporomandibular), knuckle, interphalangeal joint, atlanto-occipital joint, atlanto-axial joint, and intervertebral joint.

62. The method of claim 55, wherein the polysaccharide molecules comprise about 8% to about 12% by weight of the composition.

* * * * *